United States Patent [19]
Hashimoto et al.

[11] Patent Number: 5,859,294
[45] Date of Patent: Jan. 12, 1999

[54] PROCESS FOR THE PRODUCTION OF HIGH-PURITY NAPHTHALENEDICARBOXYLIC ACID

[75] Inventors: Akio Hashimoto; Ryusuke Shigematsu; Kenichi Nakamura; Makoto Takagawa, all of Ibaraki-ken, Japan

[73] Assignee: Mitsubishi Gas Chemical Corporation, Inc., Tokyo, Japan

[21] Appl. No.: 943,718

[22] Filed: Oct. 3, 1997

Related U.S. Application Data

[63] Continuation-in-part of Ser. No. 788,435, Jan. 28, 1997, abandoned.

[30] Foreign Application Priority Data

| Feb. 5, 1996 | [JP] | Japan | 8-18962 |
| Feb. 5, 1996 | [JP] | Japan | 8-18963 |
| Jun. 4, 1996 | [JP] | Japan | 8-141687 |

[51] Int. Cl.⁶ ................................. C07C 51/42
[52] U.S. Cl. ............................. 562/486; 562/487
[58] Field of Search ..................... 562/483, 485, 562/486, 487

[56] References Cited

U.S. PATENT DOCUMENTS

| 5,481,033 | 1/1996 | Alms et al. | 562/486 |
| 5,563,294 | 10/1996 | Holzhauer et al. | 562/483 |

FOREIGN PATENT DOCUMENTS

| 0 636 600 | 2/1995 | European Pat. Off. |
| 0 672 644 | 9/1995 | European Pat. Off. |
| WO94/00413 | 2/1994 | WIPO |

OTHER PUBLICATIONS

Yamamoto et al., Chemical Abstracts, Vo. 84, No. 17, 26 Apr. 1976 Abstract No. 121553a JP 75 142 542.

*Primary Examiner*—Samuel Barts
*Attorney, Agent, or Firm*—Wenderoth, Lind & Ponack, L.L.P.

[57] ABSTRACT

A process for producing a high-purity naphthalenedicarboxylic acid having an improved hue or an excellent hue from a crude naphthalenedicarboxylic acid obtained by the oxidation of dialkyl naphthalene, industrially advantageously at high yields, which comprises dissolving a crude naphthalenedicarboxylic acid obtained by the oxidation of dialkyl naphthalene in an aqueous solution containing an aliphatic amine, an alicyclic amine or acetonitrile, removing heavy metal components contained as impurities until the content of the heavy metal components based on the crude naphthalenedicarboxylic acid is 100 ppm or less, and heating the aqueous solution containing a naphthalenedicarboxylic acid amine salt to distill off the amine.

18 Claims, No Drawings

PROCESS FOR THE PRODUCTION OF HIGH-PURITY NAPHTHALENEDICARBOXYLIC ACID

This application is a continuation-in-part of now abandoned application, Ser. No. 08/788,435, filed Jan. 28, 1997, now abandoned.

FIELD OF THE INVENTION

The present invention relates to a process for the production of a high-purity naphthalenedicarboxylic acid from a crude naphthalenedicarboxylic acid obtained by the oxidation of dialkylnaphthalene. The naphthalenedicarboxylic acid is useful as a raw material for a polyethylene naphthalate resin (PEN).

PRIOR ART OF THE INVENTION

A polyester obtained by the polymerization of naphthalenedicarboxylic acid and a diol such as ethylene glycol is excellent in tensile strength and heat resistance, and it finds an industrially important use as a raw material for a film, a fiber, a bottle and the like. In particular, a polyethylene naphthalate (PEN) obtained by the polymerization of 2,6-naphthalenedicarboxylic acid and ethylene glycol is expected to find an expanded use as an industrial resin in place of polyethylene terephthalate.

Naphthalenedicarboxylic acid can be obtained by oxidizing dialkylnaphthalene with molecular oxygen in an acetic acid as a solvent in the presence of a heavy metal such as Co or Mn and a bromine compound at a high temperature under high pressure. However, the so-obtained crude naphthalenedicarboxylic acid inevitably contains hundreds to thousands ppm of the metal such as Co or Mn used as a catalyst. The crude naphthalenedicarboxylic acid further contains impurities such as formyl naphthoic acid and methyl naphthoic acid which are intermediates from the oxidation, trimellitic acid which is formed by the decomposition of a naphthalene ring, bromonaphthalenedicarboxylic acid which is formed by the addition of bromine to naphthalenedicarboxylic acid, and naphthoic acid and naphthalenetricarboxylic acid derived from impurities contained in the dialkylnaphthalene used as a raw material. Furthermore, coloring components of which the structures are not known are also contained.

When the naphthalenedicarboxylic acid containing the above impurities is used as a monomer for the polymerization with a diol, the resultant polyester is poor in physical properties such as heat resistance, mechanical strength and dimensional stability and has a low softening point. Further, there is another defect that the polyester is colored and poor in product quality.

Specifically, when monocarboxylic acids such as naphthoic acid, methyl naphthoic acid and formyl naphthoic aicd are contained in an amount over a certain limit, the polymerization degree cannot be increased, and gelation and coloring take place. It is therefore essential to decrease the above amount. That is, a high-purity naphthalenedicarboxylic acid of which the impurity content is very small is required for obtaining a polyester having a high product quality. Formyl naphthoic acid particularly has the above detrimental influence to a great extent.

Naphthalenedicarboxylic acid cannot be distilled since it is decompsed at high temperature, and it is also difficult to purify naphthalenedicarboxylic acid by general simple recrystallization since it is sparingly soluble in usual solvents. There has therefore not been established any industrial method of preparing a high-purity naphthalenedicarboxylic acid. In general practice at present, a crude naphthalenedicarboxylic acid is reacted with an alcohol such as methanol and the resultant naphthalenedicarboxylate ester is purified. However, not the naphthalenedicarboxylate ester but naphthalenedicarboxylic acid is preferred as a raw material for polyethylenenaphthalate, and it is demanded to establish the method of purifying the naphthalenedicarboxylic acid.

As a method of purifying naphthalenedicarboxylic acid by dissolving it in a solvent, U.S. Pat. No. 5,256,817 discloses a method in which water or an acetic acid aqueous solution is used as a solvent, and naphthalenedicarboxylic acid is dissolved in the solvent at a high temperature of at least 300° C., hydrogenated and purified by crystallization. The problem of this method is that a high temperature is required for dissolving a crude 2,6-naphthalenedicarboxylic acid so that naphthoic acid is formed due to a decarbonation reaction. Further, an expensive rare metal is required as a catalyst for removing formyl naphthoic acid, and there is further another problem that tetralindicarboxylic acid is formed due to the halogenation of a naphthalene ring.

JP-A-62-230747 discloses a purification method in which a crude 2,6-naphthalenedicarboxylic acid is dissolved in a solvent such as dimethylsulfoxide, dimethylacetamide or dimethylformamide to precipitate 2,6-naphthalenedicarboxylic acid by crystallization. In this method, however, it is required to use a large amount of activated carbon for decolorization. Further, a large amount of the solvent is required since the solubility of the 2,6-naphthalenedicarboxylic acid in the solvent is low. Furthermore, it is difficult to carry out the hydrogenation since the solvent is hydrogenated as well when the solution is hydrogenated, and it is difficult to remove formyl naphthoic acid which has a detrimental effect on the polymerization. Moreover, the yield of the purified naphthalenedicarboxylic acid is low.

JP-A-5-32586 discloses a method in which crude 2,6-naphthalenedicarboxylic acid is dissolved in pyridine or a pyridine derivative to precipitate 2,6-naphthalenedicarboxylic acid by crystallization. Since, however, the dependency of the solubility of the 2,6-naphthalenedicarboxylic acid upon temperature is low, the yield thereof is low.

Besides the above methods in which naphthalenedicarboxylic acid is directly purified, there have been proposed purification methods in which crude 2,6-naphthalenedicarboxylic acid is converted to an alkali salt by dissolving it in an alkali, to improve the solubility of the 2,6-naphthalenedicarboxylic acid. For example, JP-B-52-20993 and JP-B-48-68554 disclose a method in which crude naphthalenedicarboxylic acid is dissolved in an alkaline aqueous solution of KOH or NaOH and treated with a solid adsorbent, then, naphthalenedicarboxylic acid is precipitated in the form of a monoalkali salt with an acid such as a carbon dioxide gas or a sulfurous acid gas, and the monoalkali salt is brought into contact with water to cause disproportionation thereby to free the 2,6-naphthalenedicarboxylic acid. However, the above method has defects that a large amount of a solid adsorbent is required for discoloration and further that salts of impurities such as 2,6-formyl naphthoic acid, etc., are concurrently precipitated when the monoalkali salt is precipitated. There is also another defect that the alkali and the acid in large amount should be treated or recovered.

JP-B-52-20994 and JP-B-48-68555 disclose a method in which crude 2,6-naphthalenedicarboxylic acid is dissolved in an alkaline aqueous solution of KOH or NaOH, the treatment for discoloration with a solid adsorbent is carried out, then, a dialkali salt is crystallized by cooling or concentration, and further, the dialkali salt is disproportionated to obtain a purified 2,6-naphthalenedicarboxylic acid. However, the above method has the following defects. A solid adsorbent is required for discoloration. The yield of 2,6-naphthalenedicarboxylic acid is low since the dependency of solubility of the dialkali salt upon temperature is low and since the solubility of the dialkali salt in water at a low temperature is very high. Further, a very small amount of an alkali is contained in the purified crystal, and it is difficult to remove the alkali.

JP-A-2-243652 discloses a purification method in which crude 2,6-naphthalenedicarboxylic acid is dissolved in an alkaline aqueous solution, and an organic solvent having a high solubility in water such as an alcohol or acetone is added to precipitate a crystal of a dialkali salt of 2,6-naphthalenedicarboxylic acid. In the above method, however, the precipitation rate of the crystal is high so that impurities are liable to be included, and when the yield is high, the effect on the removal of impurities is insufficient.

There have been also proposed a variety of purification methods using an amine. JP-A-50-135062 discloses a method in which crude 2,6-naphthalenedicarboxylic acid is dissolved in an aqueous solution of an aliphatic amine having 6 carbon atoms or less, the solution is cooled or concentrated to precipitate 2,6-naphthalenedicarboxylic acid in the form of a diamine salt and the diamine salt is decomposed under heat to obtain 2,6-naphthalenedicarboxylic acid. Since, however, the yield is low because of the very high solubility of the diamine salt in water at a low temperature, the above method is impractical in industry.

JP-A-5-294892 discloses a method in which naphthalenedicarboxylic acid is dissolved in mixed solvents of an amine and an alcohol to precipitate a crystal of a naphthalenedicarboxylic acid amine salt, and the crystal is decomposed under heat at a temperature equivalent to, or higher than, the boiling point of the amine, to obtain a purified naphthalenedicarboxylic acid. The above method as well has a defect that the yield of naphthalenedicarboxylic acid is low since the solubility of the naphthalenedicarboxylic acid amine salt in a lower alcohol is high.

JP-A-50-142542 discloses a method in which crude 2,6-naphthalenedicarboxylic acid is dissolved in an amine aqueous solution, and then an amine compound is distilled off and 2,6-naphthalenedicarboxylic acid is precipitated to obtain a purified 2,6-naphthalenedicarboxylic acid.

In the above method, a large amount of water is used, and a large amount of energy is consumed. Further, the yield of 2,6-naphthalenedicarboxylic acid in Examples is as low as 63.8 to 72.4%. Further, when the present inventors closely studied the above method of JP-A-50-142542, no 2,6-naphthalenedicarboxylic acid having a sufficiently good hue could be obtained when the yield of 2,6-naphthalenedicarboxylic acid is sufficient for industrial practice.

As explained above, in the above conventional methods of purifying naphthalenedicarboxylic acid in the presence of an amine, it is required to heat-decompose or distill off the amine compound, and the naphthalenedicarboxylic acid is therefore exposed to high temperatures. The coloring of the naphthalenedicarboxylic acid is accordingly promoted, and it is therefore difficult to obtain naphthalenedicarboxylic acid as a product having a high quality. Further, since the yield of naphthalenedicarboxylic acid is generally low, it is demanded to overcome the above defects.

SUMMARY OF THE INVENTION

It is an object of the present invention to provide a process for producing a high-purity naphthalenedicarboxylic acid having an improved hue or an excellent hue from a crude naphthalenedicarboxylic acid obtained by the oxidation of dialkyl naphthalene, industrially advantageously at high yields.

It is another object of the present invention to provide a process for producing a high-purity naphthalenedicarboxylic acid of which methyl naphthoic acid and formyl naphthoic acid contents are small, from the above crude naphthalenedicarboxylic acid, industrially advantageously at high yields.

According to the present invention, there is provided a process for the production of a high-purity naphthalenedicarboxylic acid, which comprises dissolving a crude naphthalenedicarboxylic acid obtained by the oxidation of dialkyl naphthalene in an aqueous solution containing an aliphatic or alicyclic amine, removing heavy metal components contained as impurities until the content of the heavy metal components based on the crude naphthalenedicarboxylic acid is 100 ppm or less, and heating the aqueous solution containing a naphthalenedicarboxylic acid amine salt to provide a high-purity naphthalenedicarboxylic acid by distilling off the amine.

According to the present invention, further, there is provided a process for the production of a high-purity naphthalenedicarboxylic acid, which comprises dissolving a crude naphthalenedicarboxylic acid obtained by the oxidation of dialkyl naphthalene in an aqueous solution containing an aliphatic or alicyclic amine, bringing the aqueous solution into contact with a metal belonging to the group VIII of the periodic table in an inert gas atmosphere, and heating the aqueous solution containing a naphthalenedicarboxylic acid amine salt to provide a high-purity naphthalenedicarboxylic acid by distilling off the amine.

Further, according to the present invention, there is provided a process for the production of a high-purity naphthalenedicarboxylic acid, which comprises dissolving a crude naphthalenedicarboxylic acid obtained by the oxidation of dialkyl naphthalene in an aqueous solution containing an aliphatic amine, an alicyclic amine or an acetonitrile, precipitating a crystal of a naphthalenedicarboxylic acid amine salt in mixed solvents of water with an aliphatic ketone, an alicyclic ketone or an acetonitrile, and heating the amine salt of the naphthalenedicarboxylic acid to provide a high-purity naphthalenedicarboxylic acid by distilling off the amine.

DETAILED DESCRIPTION OF THE INVENTION

The present invention 1 is directed to a process for the production of a high-purity naphthalenedicarboxylic acid, which comprises dissolving a crude naphthalenedicarboxylic acid obtained by the oxidation of dialkyl naphthalene in an aqueous solution containing an aliphatic or alicyclic amine, removing heavy metal components contained as impurities until the content of the heavy metal components based on the crude naphthalenedicarboxylic acid is 100 ppm or less, and heating the aqueous solution containing a naphthalenedicarboxylic acid amine salt to distill off the amine. The present invention 1 provides a production process in which heavy metal components are removed so that the naphthalenedicarboxylic acid is no longer deteriorated in hue in subsequent steps. In the present invention, after the removal of heavy metal components, decarbonylation, hydrogenation, crystallization in mixed solvents of water and a ketone compound and other treatment can be properly carried out as required.

The present invention 2 is directed to a process for the production of a high-purity naphthalenedicarboxylic acid, which comprises dissolving a crude naphthalenedicarboxylic acid obtained by the oxidation of dialkyl naphthalene in an aqueous solution containing an aliphatic or alicyclic amine, bringing aldehyde compounds contained as impurities in the aqueous solution into contact with a metal belonging to the group VIII of the periodic table in an inert gas atmosphere, thereby causing a decarbonylating reaction to convert the aldehyde compounds to naphthoic acid, and heating the aqueous solution containing a naphthalenedicarboxylic acid amine salt to distill off the amine. The present invention 2 provides a high-purity naphthalenedicarboxylic acid of which the methyl naphthoic acid and formyl naphthoic acid contents are small. When formyl naphthoic acid, etc., are contained in an amount larger than a certain limit, the polymerization degree cannot be increased, and gelation and coloring take place to deteriorate the product (polyester) quality.

The present invention 3 is directed to a process for the production of a high-purity naphthalenedicarboxylic acid, which comprises dissolving a crude naphthalenedicarboxylic acid obtained by the oxidation of dialkyl naphthalene in an aqueous solution containing an aliphatic amine, an alicyclic amine or an acetonitrile, precipitating a crystal of a naphthalenedicarboxylic acid amine salt in mixed solvents of water with an aliphatic ketone, an alicyclic ketone or acetonitrile, and heating the naphthalenedicarboxylic acid amine salt to distill off the amine. The present invention 3 provides a high-purity naphthalenedicarboxylic acid which is almost completely free of organic impurities, monocarboxylic acids in particular, and is excellent in hue.

The crude naphthalenedicarboxylic acid used as a raw material in the present invention is not specially limited so long as it is obtained by the oxidation of dialkyl naphthalene.

The dialkyl naphthalene used for the oxidation includes dimethyl naphthalene, diethyl naphthalene, dipropyl naphthalene and diisopropyl naphthalene. Each of these dialkyl naphthalenes has 10 isomers with regard to the positions of alkyl groups. For a raw material for the polyester, 2,6-substituted naphthalene and 2,7-substituted naphthalene are useful among the above dialkyl naphthalenes, and 2,6-naphthalenedicarboxylic acid is particularly preferred. The above dialkyl naphthalenes are oxidized with molecular oxygen in the presence of an oxidation catalyst formed mainly of a heavy metal and bromine, to give crude naptalenedicarboxylic acids.

Examples of the aliphatic or alicyclic amine (to be sometimes referred to as "amine" or "amine compound" hereinafter) used for forming the crude naphthalenedicarboxylic acid amine salt are as follows.

Aliphatic amines such as methylamine, dimethylamine, trimethylamine, ethylamine, diethylamine, triethylamine, ethyldimethylamine, diethylmethylamine, propylamine, isopropylamine, dipropylamine, diisopropylamine, butylamine, isobutylamine, sec-butylamine, tert-butylamine, dibutylamine, diisobutylamine, tributylamine, pentylamine, dipentylamine, tripentylamine and 2-ethylhexylamine; and alicyclic amines such as piperidine, N-methylpyridine, pyrrolidine, ethylimine and hexamethyleneimine.

Of the above amines, methylamines and ethylamines are preferred in view of easiness in handling and availability, and trimethylamine and triethylamine are particularly preferred since these give amine salts having low decomposition temperatures when naphthalenedicarboxylic acid amine salts are formed. Further, the above amines may be used alone or in combination.

In the process of the present invention, first, the crude naphthalenedicarboxylic acid is dissolved in an aqueous solution containing the above amine. The amine compound is preferably used in an equivalent weight equivalent to, or greater than, the equivalent weight of the crude naphthalenedicarboxylic acid. For economic performance in industry, the amount of the amine compound is 1.0 to 1.2 equivalent weights per equivalent weight of carboxyl groups.

The amount of water differs depending upon the kind and amount of the amine, the temperature at which the crude naphthalenedicarboxylic acid is dissolved and the kind and amount of contained impurities. Generally, the amount of water is 0.5 to 50 times, preferably 1 to 20 times, the weight of the naphthalenedicarboxylic acid.

The temperature employed for dissolving the crude naphthalenedicarboxylic acid in an aqueous solution containing the above amine to form an amine salt is approximately 10° to 100° C.

In the present invention 1, before the procedure of distilling the amine off is carried out, it is required to remove heavy metal components contained as impurities in the aqueous solution containing the amine salt until the content of the impurities is 100 ppm or less based on the naphthalenedicarboxylic acid. When the content of the impurities is higher than 100 ppm, the naphthalenedicarboxylic acid as an end product is poor in hue, and it is much more colored than the crude naphthalenedicarboxylic acid as a raw material. This occurs regardless of yields of the naphthalenedicarboxylic acid as an end product, and even if the yield is decreased, the naphthalenedicarboxylic acid is inevitably colored.

The reason for the above coloring is that the heavy metal components contained as impurities promote the new formation of coloring components when the amine is distilled off. When the mere treatment of adsorption with a solid adsorbent is carried out as described in JP-A-52-142542, it is possible to remove isomers and bromine derivatives of naphthalenedicarboxylic acid, aldehydes and originally existing coloring components which are contained as impurities. However, the heavy metal components cannot be always removed until the content thereof is 100 ppm or less, and it is difficult to prevent the new formation of coloring components at a time of distilling off the amine. In the present inventions 2 and 3, preferably, the procedure of removing the heavy metal components is carried out in advance.

With a decrease in the content of the heavy metal components, the new formation of coloring components is better prevented. When the above content exceeds 100 ppm, the coloring takes place to a great extent. It is therefore required to remove the heavy metal components until the content thereof is 100 ppm or less.

The heavy metal components contained in the crude naphthalenedicarboxylic acid are mainly cobalt and manganese which are components of a catalyst used for the oxidation of dialkyl naphthalene, and besides these, there are metal components which are from a co-catalyst and titanium, iron, nickel, chromium, and the like which are from materials of a reactor. The crude naphthalenedicarboxylic acid contains hundreds to thousands ppm of cobalt and manganese, and it is particularly essential to remove them.

When the crude naphthalenedicarboxylic acid is dissolved in an amine aqueous solution, most of the above heavy metal components are precipitated as insolubles. The insoluble heavy metal components are first removed by filtration. The opening diameter of a filter used for the filtration is 10 $\mu$m or less, preferably 5 $\mu$m or less, more preferably 1 $\mu$m or less. In an industrial apparatus, it is preferred to employ a multi-stage filter of which the opening diameters are stepwise decreased, for preventing the clogging and securing a stable operation for a long period of time.

Those heavy metal components which are not removable through the above filter(s) can be removed by adsorption with a solid adsorbent. The solid adsorbent is selected from activated carbon, activated alumina, activated clay or an ion-exchange resin. When the solid adsorbent is used with an industrial apparatus, a column is packed with the solid adsorbent, and an aqueous solution containing a naphthalenedicarboxylic acid amine salt is continuously fed to the column.

When the removal of the heavy metal components is carried out by directly feeding the amine aqueous solution to a column packed with the solid adsorbent without carrying out the filtering operation in advance, the solid adsorbent is overloaded since the amount of the insoluble heavy metal components to be removed is too large, and there is obtained no continuous effect on the removal of the heavy metal components in the operation for a long period of time. Further, since a large amount of the heavy metal components deposit in the column and clog the column, no stable continuous operation is possible.

When the adsorption with the solid adsorbent is carried out by a batch method, it is required to separate the amine aqueous solution and solid components by filtration, and in this case, undesirably, the amount of the solid components which are to be treated is large as compared with the amount of solid components which are filtered off in the beginning.

Then, it is preferred to remove formyl naphthoic acid, of which the presence causes a problem at a polymerization time, from the aqueous solution containing a the naphthalenedicarboxylic acid amine salt from which the heavy metal components are removed until the content thereof is 100 ppm or less.

For removing the above formyl naphthoic acid, generally, a rare metal catalyst is used, and the rare metal catalyst is doped with the heavy metal components. By removing the heavy metal components until the content thereof is 100 ppm or less, the life of the catalyst used for removing formyl naphthoic acid before the amine is distilled off can be maintained for a long period of time.

The formyl naphthoic acid is removed, for example, by hydrogenating treatment, in which the formyl group of the formyl naphthoic acid is converted to a methyl group. As a catalyst for the hydrogenation, there is used a catalyst prepared by dispersing at least one selected from Pt, Pd, Rh, Ru, Ni or Co on a carrier having a large surface area such as activated carbon, silica or alumina. It is preferred to use a catalyst prepared by dispersing Pd or Pt on activated carbon. For removing the naphthoic acid, the solution prepared by dissolving the crude naphthalenedicarboxylic acid in the amine aqueous solution is subjected to hydrogenation in the presence of the above catalyst. The hydrogenation may be carried out by any one of a batch method and a continuous flow method. The continuous flow method is industrially preferred. The hydrogenation conditions differ depending upon the kind and amount of the catalyst and the residence time. Generally, the hydrogenation temperature is 70° to 250° C. The hydrogen partial pressure is 0.01 to 30 kg/cm$^2$, preferably 0.01 to 10 kg/cm$^2$. When the hydrogenation is carried out under severe conditions at 250° C. or higher, tetralindicarboxylic acid may be formed since the ring of the naphthalene is hydrogenated as a side reaction, or naphthoic acid may be formed due to decarbonation or decarbonylation.

As described in the present invention 1, decarbonylation may be carried out after the heavy metal components are removed. As described in the present invention 2, decarbonylation may be carried out without removing the heavy metal components.

The formyl naphthoic acid contained as impurity is converted to naphthoic acid by the decarbonylation, and it can be therefore removed. When the hydrogenation is carried out without carrying out the decarbonylation, methyl naphthoic acid is formed from the formyl naphthoic acid, and the methyl naphthoic acid is precipitated together with naphthalenedicarboxylic acid when the amine aqueous solution is heated to distill off the amine. As a result, the methyl naphthoic acid cannot be removed.

It is therefore useless to carry out the decarbonylation after the hydrogenation. The formyl naphthoic acid can be removed by the decarbonylation alone without carrying out the hydrogenation depending upon the kind and amount of impurities contained in the crude naphthalenedicarboxylic acid. Further, usually contained naphthalenedicarboxylic acid bromide can be removed by the decarbonylation.

The decarbonylation is carried out in the presence of a catalyst prepared by dispersing at least one selected from Pt, Pd, Rh, Ru, Ni or Co on a carrier having a large surface area such as activated carbon, silica or alumina. It is preferred to use a catalyst prepared by dispersing Pd or Pt on activated carbon.

The decarbonylation is carried out by bringing the above catalyst and the amine aqueous solution of the crude naphthalenedicarboxylic acid into contact with each other in an inert gas atmosphere. The term "inert gas" refers to a gas which is inert to the decarbonylation and substantially does not contain hydrogen. The concentration of hydrogen in the inert gas does not exceed 10 ppm. The inert gas includes nitrogen, argon and helium, while a nitrogen gas is generally used.

The decarbonylation may be carried out by any one of a batch method and a continuous flow method, while the continuous flow method is industrially preferred. The pressure for the decarbonylation is not specially limited. The temperature for the decarbonylation differs depending upon the kind and amount of the catalyst and the residence time, while it is generally 70° to 250° C. When the decarboxylation is carried out under severe conditions at 250° C. or higher, a coloring substance may be formed by a side reaction.

When the aqueous solution containing a the naphthalenedicarboxylic acid amine salt, which has been subjected to the decarbonylation, still contains formyl naphthoic acid and naphthalenedicarboxylic acid bromide in an amount larger than the allowable limit, the aqueous solution is subjected to hydrogenation to remove the above impurities. A catalyst similar to the catalyst used for the decarbonylation can be used for the above hydrogenation.

The process of the present invention includes two embodiments; in one embodiment, the decarbonylation is carried out with one reactor, and in the other embodiment, two reactors are connected in series, the decarbonylation is carried out in one reactor and the hydrogenation is carried out in the other reactor. The decarbonylation and the hydrogenation may be separately carried out in one reactor through an intermediate portion of which a hydrogen gas is introduced.

As compared with a conventional case where the purification is carried out by hydrogenation alone, the present invention which carries out the decarbonylation gives an excellent effect on the purification.

In the present invention, the precipitation by crystallization may be carried out after the removal of the heavy metal components as described in the present invention 1, and the naphthalenedicarboxylic acid amine salt may be crystallized without removing the heavy metal components as is described in the present invention 3.

The present inventors have found the following. When the aliphatic or alicyclic amine salt of the crude naphthalenedicarboxylic acid is crystallized in mixed solvents of water with an aliphatic ketone, alicyclic ketone or an acetonitrile, there can be obtained a naphthalenedicarboxylic acid amine salt which is nearly completely free of organic impurities, monocarboxylic acids in particular, and is improved in hue. When the above mixed solvents are used, the dependency of solubility of the above amine salt upon temperature is high, and 2,6-naphthalenedicarboxylic acid amine salt can be therefore recovered at high yields. When the amine is distilled off by heating the recovered naphthalenedicarboxylic acid amine salt, a high-purity naphthalenedicarboxylic acid excellent in hue can be obtained at high yields.

In the present invention 3, the purification of the crude naphthalenedicarboxylic acid comprises the step of crystallizing a crude naphthalenedicarboxylic acid amine salt from mixed solvents of water with an aliphatic ketone, alicyclic ketone or an acetonitrile and the step of heating the naphthalenedicarboxylic acid amine salt, which is purified by the crystallization, to distill off the amine.

The aliphatic or alicyclic ketone (to be sometimes simply referred to as "ketone" hereinafter) used in the present invention are as follows.

Aliphatic ketones such as acetone, methyl ethyl ketone, methyl propyl ketone, diethyl ketone, methyl n-butyl ketone, methyl isobutyl ketone, 2-heptanone, 4-heptanone, diisobutyl ketone and acetonyl acetone; and alicyclic ketones such as cyclohexanone and methylcyclohexanone.

Of the above ketones, acetone is particularly preferred since the dependency of solubility of the above amine salt upon temperature is the highest when it is mixed with water and since it is easy in handling and availability.

The above ketones may be used alone or in combination.

In the crystallization step, first, the crude naphthalenedicarboxylic acid amine salt is mixed with the mixed solvents of water with the ketone or an acetonitrile, and the resultant mixture is heated. By this procedure, the crude naphthalenedicarboxylic acid amine salt is dissolved in the mixed solvents of water with the ketone or an acetonitrile. The crude naphthalenedicarboxylic acid may be added to the mixed solvents containing the amine, water and the ketone or an acetonitrile.

In the above crystallization of the naphthalenedicarboxylic acid amine salt, the water/ketone amount ratio of the mixed solvents is 1 to 99 parts by weight/99 to 1 part by weight, preferably, 3 to 15 parts by weight/97 to 85 parts by weight. In the above crystallization of the naphthalenedicarboxylic acid amine salt, the water/acetonitrile amount ratio of the mixed solvents is 1 to 99 parts by weight/99 to 1 part by weight, preferably, 3 to 25 parts by weight/97 to 75 parts by weight.

The naphthalenedicarboxylic acid amine salt shows a high solubility in water alone. However, the dependency of the solubility upon water is low, and the solubility is high even at a low temperature. In the crystallization in water alone, therefore, the yield of a crystal of the naphthalenedicarboxylic acid amine salt is low. Further, the naphthalenedicarboxylic acid amine salt has almost no solubility in the ketone or an acetonitrile alone, and the crystallization is therefore impossible. In contrast, the present inventors have found a phenomenon that when mixed solvents of water with the ketone or acetonitrile are used, the naphthalenedicarboxylic acid amine salt is well dissolved at a high temperature, and the solubility at a low temperature is low.

The solubility of 2,6-naphthalenedicarboxylic acid (2,6-NDCA-TEA) triethylamine salt was measured in water-acetone mixed solvents having a water concentration below. Table 1 shows the results.

TABLE 1

| Solubility[g-2,6-NDCA- | Water concentration (wt %) in water/acetone mixed solvents | | | |
|---|---|---|---|---|
| TEA/100 g solvents] | 5 | 10 | 20 | 100 |
| 25 (°C.) | 0.5 or less | 1.2 | 9.5 | 110 |
| 50 (°C.) | 1.0 | 4.4 | 23 | 135 |
| 75 (°C.) | 6 | 17 | 64 | 204 |
| 100 (°C.) | 30 | 63 | 170 | 240 |

For example, 60 g of the ditriethylamine salt of 2,6-naphthalenedicarboxylic acid is dissolved in 100 g of the mixed solvents having a water concentration of 10 wt % at 100° C., and then the mixture is cooled to 25° C. In this case, the amount of the 2,6-naphthalenedicarboxylic acid triethylamine salt dissolved at 25° C. is 1.2 g, and a crystal of the diethyltriethylamine salt of 2,6-naphthalenedicarboxylic acid is precipitated at a recovery of 98% [(60−1.2)/60=0.98].

It is the most preferred to use acetone as a ketone. When 10 wt % water/methyl ethyl ketone mixed solvents or 10 wt % water/cyclohexanone mixed solvents are used, the dependency of solubility of the amine salt upon temperature is smaller than the dependency when the 10 wt % water/acetone mixed solvents are used.

Further, the solubility of 2,6-naphthalenedicarboxylic acid (2,6-NDCA-TEA) triethylamine salt, which is obtained when an triethylamine used as the amine, was measured in water-acetonitrile mixed solvents having a water concentration of 5,10 or 20% by weight and measured in water. Table 2 shows the results.

TABLE 2

| Solubility[g-2,6-NDCA- | Water concentration (wt %) in water/acetonitrile mixed solvents | | | |
|---|---|---|---|---|
| TEA/100 g solvents] | 5 | 10 | 20 | 100 |
| 25 (°C.) | 0.7 | 4.3 | 11 | 110 |
| 50 (°C.) | 4.0 | 14 | 44 | 135 |
| 75 (°C.) | 22 | 45 | 90 | 204 |
| 100 (°C.) | 110 | 140 | 170 | 240 |

For example, 140 g of the ditriethylamine salt of 2,6-naphthalenedicarboxylic acid is dissolved in 100 g of the water-acetonitrile mixed solvents having a water contentration of 10 wt % at 100° C., and then the mixture is cooled to 25° C. for crystallization. In this case, the amount of the 2,6-naphthalenedicarboxylic acid triethylamine salt dissolved at 25° C. is 4.3 g, and a crystal of the diethyltriethylamine salt of 2,6-naphthalenedicarboxylic acid is precipitated at a recovery of 97% [(140−4.3)/140=0.97].

When above mixed solvents containing water and the ketone or acetonitrile are used, the crystallization of the naphthalenedicarboxylic acid amine salt at a high recovery ratio, which has been impossible when water alone, the ketone alone or acetonitrile alone is used, can be accomplished.

When the crude naphthalenedicarboxylic acid and the amine or acetonitrile are mixed in the above mixed solvents under heat, the naphthalenedicarboxylic acid amine salt is readily formed and dissolved in the mixed solvents. The amount of the above amine is equivalent to, or greater than, the equivalent weight of carboxyl groups of the crude naphthalenedicarboxylic acid. For carrying out the above crystallization industrially economically, the amount of the amine based on the above carboxyl groups is properly 1.0 to 1.2 equivalent weights.

The amount of the mixed solvents of which the water/ketone or water/acentonitrile ratio is specified already is 0.2 to 100 times, preferably 0.5 to 10 times, the amount of the crude naphthalenedicarboxylic acid. The amount and the ratio of the water/ketone or water/acentonitrile mixed solvents are adjusted in the above ranges depending upon the crystallization temperature, the recovery and purification degree of the naphthalenedicarboxylic acid amine salt and the operability and economic performance in a solid/liquid separation.

The temperature at which the crude naphthalenedicarboxylic acid and the mixed solvents of water with the ketone or an acetonitrile are mixed and the naphthalenedicarboxylic acid amine salt is formed and dissolved is 0° to 250° C., preferably 50° to 150° C. The pressure in the reaction system in this case is dependent upon the amount ratio and the temperature of the mixed solvents, and it is not specially limited.

In the above operation, the heavy metal components such as Co, Mn, etc., derived from an oxidation catalyst, are precipitated as insolubles in a solution of the crude naphthalenedicarboxylic acid amine salt in the mixed solvents of water with the ketone or acetonitrile. For obtaining a purified naphthalenedicarboxylic acid having a high quality, it is preferred to remove the above heavy metal components by filtration. Further, the heavy metal components may be removed by filtration by dissolving the naphthalenedicarboxylic acid amine salt in a solvent such as water before the step of distilling off the amine by heating the naphthalenedicarboxylic acid amine salt purified by the crsytallization.

Then, a solution of the naphthalenedicarboxylic acid amine salt in the mixed solvents of water with the ketone or acetonitrile is subjected to crystallization, whereby a purified crystal of the naphthalenedicarboxylic acid amine salt is obtained. The crystallization is carried out by precipitating the naphthalenedicarboxylic acid amine salt on the basis of the dependency of solubility of the amine salt upon temperature, i.e., by providing a temperature difference or cooling the solution.

The temperature to which the solution is cooled ("cooling temperature" hereinafter) is in the range of from −50° to 100° C. Generally preferably, the cooling temperature which can be industrially easily employed is approximately 10° to 60° C. In the present invention, the solubility of the naphthalenedicarboxylic acid amine salt in the mixed solvents around room temperature is low, and the dependency of the solubility upon temperature is high. In the crystallization at the cooling temperature in the above range, therefore, a naphthalenedicarboxylic acid amine salt having a sufficient purification degree can be obtained with a high recovery in an economical amount of the mixed solvents.

By the above procedure, organic impurities contained in the crude naphthalenedicarboxylic acid are almost all removed. In particular, monocarboxylic acids such as naphthoic acid, methyl naphthoic acid and formyl naphthoic acid are nearly completely removed. The process of the present invention obviates the particular procedure for the removal of formyl naphthoic acid such as hydrogenation or the like, since formyl naphthoic acid which is liable to remain in the procedure of general crystallization is removed.

In the above crystallization, further, coloring components contained in the crude naphthalenedicarboxylic acid are also removed, and a naphthalenedicarboxylic acid amine salt having a remarkably improved hue can be obtained.

For further discoloration, the naphthalenedicarboxylic acid amine salt can be treated with a solid adsorbent. For example, the above naphthalenedicarboxylic acid amine salt obtained by the crystallization is re-dissolved in a solvent such as water, and the resultant solution is subjected to a discoloration treatment with a solid adsorbent. Further, the above amine salt may be subjected to a purification treatment such as hydrogenation. It is uneconomical to carry out the adsorption with a solid adsorbent before the crystallization, since the adsorbent is overloaded by the discoloration so that a large amount of the solid adsorbent is required.

In the present invention, the crystallization can be carried out by any one of a batch method and a continuous flow method, while a continuous flow method is superior when a large amount of the naphthalenedicarboxylic acid amine salt is treated in an industrial process. The naphthalenedicarboxylic acid amine salt is isolated by a solid-liquid separation operation such as filtration or centrifugal separation.

Then, the above-obtained crystal is washed with a solvent which is soluble in water and the ketone or acetonitrile but has almost no solubility in the naphthalenedicarboxylic acid amine salt, for removing the crystallization mother liquor adhering the crystal surface. Generally, a ketone alone is used or a ketone containing a small amount of water is used as a solvent for the above washing. The crystallization mother liquor and the wash liquid are recycled as a crystallization raw material, directly or after impurities are removed.

When the above crystallization is carried out a plurality of times, there can be obtained a naphthalenedicarboxylic acid amine salt having a higher purity and a more improved hue, while the number of times with which the crystallization is carried out is determined by considering the purification degree of the amine salt and economic performance.

According to the present invention 1 and invention 2, an amine compound is distilled off from an aqueous solution containing the above-obtained naphthalenedicarboxylic acid amine salt. The method of distilling off the amine compound includes a method in which the amine aqueous solution is externally heated to distill off amine alone or amine and water, a method in which the amine aqueous solution is heated with feeding overheated steam or water, to distill off the amine compound, a method in which amine is distilled of f with blowing an inert gas such as nitrogen gas into the amine aqueous solution, and a method in which amine is distilled off under reduced pressure. Amine alone or amine and water may be distilled off by combining at least two of the above methods.

The temperature for distilling off amine is preferably at least 50° C., particularly preferably at least 80° C., since the decomposition rate of the amine salt is low when the above temperature is too low. On the other hand, when the above temperature is too high, the naphthalenedicarboxylic acid may be altered or colored. The above temperature therefore preferably does not exceed 300° C., particularly preferably, it does not exceed 250° C.

The amine compound is distilled off from the aqueous solution containing a the naphthalenedicarboxylic acid amine salt by the above method, whereby a the naphthalenedicarboxylic acid amine salt is decomposed. The so-formed amine is collected by cooling and a nearly total amount thereof can be recovered. The collected amine can be purified as required, and re-used.

As the amine is distilled off, free naphthalenedicarboxylic acid is precipitated from the aqueous solution containing the naphthalenedicarboxylic acid amine salt. The amount of the precipitated naphthalenedicarboxylic acid is in proportion to the amount of the amine which is distilled off. The naphthalenedicarboxylic acid can be obtained at a high recovery by increasing the distillation amount of the amine. Preferably, the distillation is carried out at a recovery of at least 90% for achieving an economical industrial process.

The purified naphthalenedicarboxylic acid which is precipitated by heating can be recovered by an operation such as filtration or centrifugal separation. Further, the crystal of the purified naphthalenedicarboxylic acid may be washed with water as required to remove impurities adhering to the crystal surface. Further, the so-obtained crystal is dried to give a high-purity naphthalenedicarboxylic acid.

The naphthalenedicarboxylic acid amine salt obtained by the crystallization method in the present invention 3 is also fed to the step of distilling off the amine to obtain a purified naphthalenedicarboxylic acid. The method of distilling off the amine from a the naphthalenedicarboxylic acid amine salt includes a method in which the naphthalenedicarboxylic acid amine salt is directly heated and a method in which the naphthalenedicarboxylic acid amine salt is heated in the co-presence of a solvent. Either method may be used. In the method in which a the naphthalenedicarboxylic acid amine salt is directly heated, however, organic impurities which cannot be removed in the crystallization step still remains in the crystal.

On the other hand, preferred is the method in which the naphthalenedicarboxylic acid amine salt is heated in the co-presence of a solvent to distill off the amine, since the above method has an effect that the organic impurities which cannot be removed in the crystallization step are further removed, so that a purified naphthalenedicarboxylic acid having a high product quality can be obtained. The above solvent is not specially limited so long as it has no reactivity with the naphthalenedicarboxylic acid amine salt at a heating time, while water is preferred.

In the method of distilling off the amine in the co-presence of water as a solvent, a the naphthalenedicarboxylic acid amine salt purified by the crystallization is dissolved in water. In this case, the resultant solution can be treated with a small amount of a solid adsorbent to promote discoloration. Further, the above solution can be subjected to microfiltration to remove foreign substance and metal components. Then, the above solution is heated to distill off the amine together with water. The heating method is the same as the above-described method of distilling the amine.

According to the present invention 1, the crude naphthalenedicarboxylic acid obtained by the oxidation of dialkyl naphthalene is dissolved in an aqueous solution containing the aliphatic amine to remove the heavy metal components, and then the aqueous solution is heated to distill off the amine. As a result, a high-purity naphthalenedicarboxylic acid having an excellent hue can be easily obtained at a high recovery. Further, the aqueous solution is subjected to hydrogenation after the removal of the heavy metal components, and then the amine is distilled off. As a result, formyl naphthoic acid which is to be a problem in polymerization is removed, and the hydrogenation catalyst is improved in life, so that a high-purity naphthalenedicarboxylic acid can be industrially very advantageously produced. The present invention therefore has a remarkably great significance in industry.

According to the present invention 2, the crude naphthalenedicarboxylic acid obtained by the oxidation of dialkyl naphthalene is dissolved in an aqueous solution containing an aliphatic amine, the resultant aqueous solution is subjected to decarbonylation or both decarbonylation and hydrogenation, and then the aqueous solution is heated to distill off the amine. As a result, a naphthalenedicarboxylic acid almost free of methyl naphthoic acid and formyl naphthoic acid can be easily obtained at high yields.

The present invention 3 has the following features 1) to 3).

1) The crystallization is carried out in mixed solvents of water with an aliphatic ketone, an alicyclic ketone or an acetonitrile. As a result, organic impurities are almost completely removed, and an amine salt of naphthalenedicarboxylic acid having an excellent hue can be obtained.

2) The dependency of solubility of the naphthalenedicarboxylic acid amine salt upon temperature is high when the above mixed solvents are used, or the above solubility is low at a low temperature and it is high at a high temperature. As a result, a purified amine salt of naphthalenedicarboxylic acid can be obtained at a high recovery by the procedure of crystallization.

3) When the above amine salt of naphthalenedicarboxylic acid is heated to distill off the amine, a high-purity naphthalenedicarboxylic acid having an excellent hue can be obtained at a high recovery.

According to the present invention, moreover, nearly the whole of the amine generated by heating the above amine salt can be easily recovered by cooling and collecting it, and it can be recycled.

Therefore, the present invention provides an industrially excellent process and is greatly significant in industry.

EXAMPLES

The present invention will be explained more in detail with reference to Examples hereinafter, while the present invention shall not be limited to these Examples.

Concerning the purity and properties of raw materials and purified naphthalenedicarboxylic acid, organic substances were methyl-esterified and analyzed by gas chromatography, and inorganic substances were wet-decomposed and analyzed by ICP spectrometry. Concerning a hue, 1 g of a sample was dissolved in 10 ml of a 1N sodium hydroxide aqueous solution and evaluated for an absorbance of light having a wavelength of 500 nm (to be abbreviated as "$OD_{500}$" hereinafter) with a 10 mm long quartz cell.

Abbreviations in Examples, Comparative Examples and Tables stand for the following.

| | |
|---|---|
| 2,6-NDCA | 2,6-naphthalenedicarboxylic acid |
| 2,6-NDCA-TEA | triethylamine salt of 2,6-naphthalenedicarboxylic acid |
| 2-NA | 2-naphthoic acid |
| 2,6-MNA | 2,6-methyl naphthoic acid |
| 2,6-FNA | 2,6-formyl naphthoic acid |
| TMAC | trimellitic acid |
| NTCA | naphthalenetricarboxylic acid |
| Br-2,6-NDCA | Bromo-2,6-naphthalenedicarboxylic acid |
| TDCA | tetralindicarboxylic acid |
| L.E. | Substance having a low boiling point |
| H.E. | Substance having a high boiling point |
| TEA | triethylamine |
| TMA | trimethylamine |

Preparation Example 1

3.8 Grams of cobalt acetate (tetrahydrate), 32.0 g of manganese acetate (tetrahydrate) and 7.43 g of hydrogen bromide (47% aqueous solution) were mixed with, and dissolved in, 1,797 g of glacial acetic acid to prepare a catalyst liquid. A 5-liter autoclave of titanium having a stirrer, a reflux condenser and a feed pump was charged with 740 g of the above catalyst liquid. The remaining portion of the catalyst liquid was mixed with 180 g of 2,6-dimethylnaphthalene, and the mixture was charged into a feed vessel and heated to dissolve the 2,6-dimethylnaphthalene, whereby a raw material liquid was prepared.

The pressure in a reaction system was adjusted to 18 kg/cm$^2$G with nitrogen, and the reaction system was heated to 200° C. with stirring. After the temperature and the pressure were stabilized, the raw material liquid and compressed air were supplied to a reactor to initiate oxidation. While the flow amount of air was adjusted such that an off-gas from the reactor had an oxygen concentration of 0.1% by volume, the raw material liquid was continuously fed over 2 hour period. After the completion of feeding of the raw material liquid, air was continuously supplied for 9 minutes.

After the reaction, the autoclave was cooled to room temperature, and a reaction product was taken out, filtered by means of suction, washed with water and with acetic acid and dried to give a crude 2,6-NDCA having a composition and a hue shown in Table 3. The crude 2,6-NDCA contained 340 ppm of Co and 2,400 ppm of Mn. The crude 2,6-NDCA was used as a raw material in the following Examples and Comparative Examples.

Example 1

A 2-liter four-necked flask formed of glass and equipped with a reflux condenser, a stirrer and a temperature measuring tube was charged with 200 g of 2,6-NDCA, 1,070 g of water and 205.9 g (1.1 equivalent weights based on 2,6-NDCA) of TEA, and the mixture was stirred for 30 minutes. Heavy metal components which precipitated without being dissolved were filtered off through a sintered metal filter having openings having a diameter of 10 µm, and then the filtrate was further filtered through a filter having openings having diameter of 5 µm to give an aqueous solution of 2,6-NDCA-TEA.

The above-prepared solution in an amount of 70 g was placed in a 300-ml autoclave formed of stainless steel and equipped with a stirrer, a pressure filter device and a gas outlet, and the atmosphere in the autoclave was replaced with nitrogen. Then, the mixture was heated up to 200° C., and while water was added at a flow rate of 100 g/hour at the same temperature, a distillate was withdrawn, at a rate equivalent to the flow rate of water, from the top of the reaction apparatus. This procedure was carried out for 2 hours. The total distilate amount was about 21 times as much as the amount of NDCA charges in the solution. The solution was filtered under pressure at the same temperature to obtain a crystal, and the crystal was washed with water and with acetic acid, and then dried under vacuum for 5 hours at 120° C., to give a purified 2,6-NDCA having a composition and a hue shown in Table 3 at a yield of 94.7% (yield based on the crude 2,6-NDCA). The so-obtained 2,6-NDCA contained 10 ppm of Co and 68 ppm of Mn.

Example 2

A purified 2,6-NDCA having a composition and a hue shown in Table 3 was obtained in the same manner as in Example 1 except that the filter having openings having a diameter of 5 µm was replaced with a nitrocellulose membrane filter having openings having a diameter of 1 µm. The so-obtained 2,6-NDCA contained less than 1 ppm of Co and 20 ppm of Mn.

Example 3

A purified 2,6-NDCA having a composition and a hue shown in Table 3 was obtained in the same manner as in Example 1 except that the filter having openings having a diameter of 5 µm was replaced with a nitrocellulose membrane filter having openings having a diameter of 1 µm and further that 70 g of the aqueous solution was flowed through a column formed of glass and packed with activated carbon to obtain an aqueous solution of 2,6-NDCA-TEA. The so-obtained 2,6-NDCA contained less than 1 ppm of Co and less than 0.5 ppm of Mn.

Example 4

A purified 2,6-NDCA having a composition and a hue shown in Table 3 was obtained in the same manner as in Example 1 except that the filter having openings having a diameter of 5 µm was replaced with a nitrocellulose membrane filter having openings having a diameter of 1 µm and further that 70 g of the aqueous solution was flowed through a column formed of glass and packed with activated clay to obtain an aqueous solution of 2,6-NDCA-TEA. The so-obtained 2,6-NDCA contained less than 1 ppm of Co and less than 0.5 ppm of Mn.

Comparative Example 1

A purified 2,6-NDCA having a composition and a hue shown in Table 4 was obtained in the same manner as in Example 1 except that an aqueous solution of 2,6-NDCA-TEA was obtained without carrying out any filtration in the step of obtaining the aqueous solution of 2,6-NDCA-TEA. The so-obtained 2,6-NDCA contained 330 ppm of Co and 2,360 ppm of Mn.

Comparative Example 2

A purified 2,6-NDCA having a composition and a hue shown in Table 4 was obtained in the same manner as in Example 1 except that an aqueous solution of 2,6-NDCA-TEA was obtained without carrying out the filtration through the filter having openings having a diameter of 5 µm in the step of obtaining the aqueous solution of 2,6-NDCA-TEA. The so-obtained 2,6-NDCA contained 210 ppm of Co and 1,620 ppm of Mn.

Example 5

A fixed-bed pressure-flow reaction apparatus having a 13 mmφ×316 mm reaction tube formed of stainless steel and packed with 5 g of a 0.5% Pd/C catalyst having an arranged diameter of 2–3 mm, a gas-liquid separator and a raw material feed pump was charged with 10 kg/cm$^2$ of mixed gases of 33.3% by volume of hydrogen and 66.7% by volume of nitrogen. While the same gases as above were flowed at a rate of 50 ml/minute, the reaction tube was maintained at 150° C., and an aqueous solution of 2,6-NDCA-TEA obtained in the same manner as in Example 4 was flowed at 30 g/hour to carry out hydrogenation.

The aqueous solution of 2,6-NDCA-TEA obtained after the hydrogenation was distilled in the same manner as in Example 1 to give a crystal of purified 2,6-NDCA having a composition and a hue shown in Table 4. The so-obtained 2,6-NDCA contained less than 1 ppm of Co and less than 0.5 ppm of Mn.

Comparative Example 3

The same aqueous solution of 2,6-NDCA-TEA as that obtained in Comparative Example 1 was subjected to hydrogenation and distillation in the same manner as in Example 5 to give a crystal of purified 2,6-NDCA having a composition and a hue shown in Table 4. The so-obtained 2,6-NDCA contained 270 ppm of Co and 2,200 ppm of Mn.

TABLE 3

| Organic substances | PEx. 1 (%) | Ex. 1 (%) | Ex. 2 (%) | Ex. 3 (%) | Ex. 4 (%) |
| --- | --- | --- | --- | --- | --- |
| 2,6-NDCA | 98.593 | 99.746 | 99.721 | 99.938 | 99.927 |
| 2-NA | 0.056 | 0.003 | 0.006 | 0.002 | 0.003 |
| 2,6-MNA | 0.010 | 0.003 | 0.002 | 0.002 | 0.002 |
| TMAC | 0.630 | 0.002 | 0.001 | 0.001 | 0.002 |
| 2,6-FNA | 0.263 | 0.210 | 0.235 | 0.020 | 0.020 |
| TDCA | 0.000 | 0.000 | 0.000 | 0.000 | 0.000 |
| L.E. | 0.097 | 0.011 | 0.009 | 0.010 | 0.015 |
| Br-2,6-NDCA | 0.165 | 0.013 | 0.012 | 0.013 | 0.015 |
| NTCA | 0.164 | 0.003 | 0.003 | 0.002 | 0.002 |
| H.E. | 0.022 | 0.014 | 0.011 | 0.012 | 0.014 |
| Total | 100.000 | 100.000 | 100.000 | 100.000 | 100.000 |
| OD$_{500}$ | 10.256 | 0.261 | 0.256 | 0.060 | 0.100 |

Pex. = Preparation Example, Ex. = Example

TABLE 4

| Organic substances | CEx. 1 (%) | CEx. 2 (%) | Ex. 5 (%) | CEx. 3 (%) |
| --- | --- | --- | --- | --- |
| 2,6-NDCA | 99.726 | 99.721 | 99.837 | 99.828 |
| 2-NA | 0.006 | 0.008 | 0.007 | 0.008 |
| 2,6-MNA | 0.002 | 0.003 | 0.120 | 0.124 |
| TMAC | 0.221 | 0.002 | 0.001 | 0.002 |
| 2,6-FNA | 0.263 | 0.231 | 0.006 | 0.006 |
| TDCA | 0.000 | 0.000 | 0.003 | 0.002 |
| L.E. | 0.012 | 0.011 | 0.011 | 0.011 |
| Br-2,6-NDCA | 0.018 | 0.011 | 0.003 | 0.002 |
| NTCA | 0.002 | 0.004 | 0.002 | 0.002 |
| H.E. | 0.012 | 0.009 | 0.012 | 0.015 |
| Total | 100.000 | 100.000 | 100.000 | 100.000 |
| OD$_{500}$ | 0.452 | 0.338 | 0.200 | 0.321 |

CEx. = Comparative Example, Ex. = Example

Preparation Example 2

A 2-liter four-necked flaks formed of glass and equipped with a reflux condenser, a stirrer and a temperature measuring tube was charged with 200 g of the crude 2,6-NDCA obtained in Preparation Example 1, 1,070 g of water and 205.9 g (1.1 equivalent weights based on 2,6-NDCA) of TEA, and these materials were stirred to obtain an aqueous solution of 2,6-NDCA-TEA. A heavy metal component, Mn, was floating as an insoluble in the aqueous solution.

Preparation Example 3

The aqueous solution of 2,6-NDCA-TEA obtained in Preparation Example 2 was filtered through a sintered metal filter having openings having a diameter of 10 μm, and the heavy metal component was removed by filtering the filtrate through a nitrocellulose membrane filter having openings having a diameter of 1 μm to prepare an aqueous solution of 2,6-NDCA-TEA. Part of the aqueous solution was taken, and water and TEA were distilled off by heating the filtrate under vacuum to obtain 2,6-NDCA. The 2,6-NDCA was dried to solidness. Table 5 shows the composition of the so-obtained 2,6-NDCA. The 2,6-NDCA contained 80 ppm of Mn.

Example 6

An autoclave formed of stainless steel and equipped with a stirrer and a pressure filtration device was charged with 100 g of the aqueous solution of 2,6-NDCA-TEA obtained in Preparation Example 3 and a 0.5% Pd/C catalyst powder, and the atmosphere in the system was replaced with nitrogen. Then, the mixture was stirred at 150° C. for 1 hour to carry out decarbonylation, allowed to cool and then filtered to obtain an aqueous solution of 2,6-NDCA-TEA.

A 300-ml autoclave formed of stainless steel and equipped with a stirrer, a pressure filtration device and a gas outlet was charged with 70 g of the above aqueous solution, and the atmosphere in the autoclave was replaced with nitrogen. The aqueous solution was heated up to 200° C., and while water was added at a flow rate of 100 g/hour at the same temperature, a distillate was withdrawn, at a rate equivalent to the flow rate of water, from the top of the reaction apparatus. This procedure was carried out for 2 hours. The total distillate amount was about 21 times as much as the amount of NDCA charges in the solution. The solution was filtered under pressure at the same temperature to obtain a crystal, and the crystal was washed with water and with acetic acid, and then dried under vacuum for 5 hours at 120° C., to give a purified 2,6-NDCA having a composition and a hue shown in Table 5 at a yield of 94.7%. The so-obtained 2,6-NDCA contained 40 ppm of 2,6-FNA and 30 ppm of 2,6-MNA.

Comparative Example 4

A crystal of purified 2,6-NDCA having a composition shown in Table 6 was obtained in the same manner as in Example 6 except that the decarbonylation was not carried out. The so-obtained 2,6-NDCA contained 20 ppm of 2,6-MNA and 2,350 ppm of 2,6-FNA.

Comparative Example 5

A crystal of purified 2,6-NDCA having a composition shown in Table 6 was obtained in the same manner as in Example 6 except that the replacement of the atmosphere in the autoclave with nitrogen was replaced with the replacement with 5 kg/cm$^2$ of hydrogen. The so-obtained 2,6-NDCA had a 2,6-FNA content of 60 ppm, while 1,230 ppm of 2,6-MNA was formed and remained.

Comparative Example 6

A crystal of purified 2,6-NDCA having a composition shown in Table 6 was obtained in the same manner as in Example 6 except that the aqueous solution of 2,6-NDCA- TEA obtained in Preparation Example 6 was replaced with the aqueous solution of 2,6-NDCA-TEA in which Mn was floating, obtained in Preparation Example 2. In the so-obtained 2,6-NDCA, the 2,6-FNA content and the 2,6-MNA content were the same as those in Example 6, while 50 ppm of Mn remained and the 2,6-NDCA was extremely colored.

Example 7

A fixed-bed pressure-flow reaction apparatus having a 13 mmφ×316 mm reaction tube formed of stainless steel and packed with 5 g of a 0.5% Pd/C catalyst having an arranged diameter of 2–3 mm, a gas-liquid separator and a raw material feed pump was internally pressure-increased with nitrogen and maintained at 10 kg/cm$^2$. While the same gas was flowed at a rate of 50 ml/minute, the reaction tube was maintained at 150° C., and an aqueous solution of 2,6-NDCA-TEA obtained in Preparation Example 3 was flowed at 30 g/hour to carry out decarbonylation.

The resultant aqueous solution of 2,6-NDCA-TEA was subjected to distillation in the same manner as in Example 6 to give a crystal of 2,6-NDCA having a composition shown in Table 5. The so-obtained 2,6-NDCA contained 40 ppm of 2,6-FNA and 20 ppm of 2,6-MNA.

Example 8

The reaction system as that used in Example 7 was internally pressure-increased with mixed gases of 33.3 vol % of hydrogen and 66.7% of nitrogen in place of nitrogen and maintained at 10 kg/cm$^2$. While the same mixed gases were flowed at a rate of 50 ml/minute, the reaction tube was maintained at 150° C., and the aqueous solution of 2,6-NDCA-TEA obtained after the decarbonylation in Example 7 was flowed at 30 g/hour to carry out hydrogenation.

The resultant aqueous solution of 2,6-NDCA-TEA was subjected to distillation in the same manner as in Example 6 to give a crystal of 2,6-NDCA having a composition shown in Table 5. The so-obtained 2,6-NDCA contained 20 ppm of 2,6-MNA, and no 2,6-MNA was detected.

Comparative Example 7

The aqueous solution of 2,6-NDCA-TEA obtained in Preparation Example 3 was subjected to the same hydrogenation and the same distillation as those in Example 8 without carrying out the decarbonylation, to give a crystal of 2,6-NDCA. The so-obtained 2,6-NDCA had a 2,6-FNA content of 50 ppm, while 1,280 ppm of 2,6-FNA was formed and remained.

TABLE 5

| Organic substance | PEx. 1 (%) | PEx. 3 (%) | Ex. 6 (%) | Ex. 7 (%) | Ex. 8 (%) |
|---|---|---|---|---|---|
| 2,6-NDCA | 98.593 | 98.593 | 99.960 | 99.955 | 99.961 |
| 2-NA | 0.056 | 0.056 | 0.005 | 0.007 | 0.006 |
| 2,6-MNA | 0.010 | 0.010 | 0.003 | 0.002 | 0.002 |
| TMAC | 0.630 | 0.630 | 0.002 | 0.003 | 0.002 |
| 2,6-FNA | 0.263 | 0.263 | 0.004 | 0.004 | 0.000 |
| TDCA | 0.000 | 0.000 | 0.000 | 0.000 | 0.002 |
| L.E. | 0.097 | 0.097 | 0.009 | 0.011 | 0.013 |
| Br-2,6-NDCA | 0.165 | 0.165 | 0.003 | 0.002 | 0.000 |
| NTCA | 0.164 | 0.164 | 0.003 | 0.0o3 | 0.002 |
| H.E. | 0.022 | 0.022 | 0.011 | 0.013 | 0.012 |
| Total | 100.000 | 100.000 | 100.000 | 100.000 | 100.000 |
| Heavy metal component | (ppm) | (ppm) | (ppm) | (ppm) | (ppm) |

TABLE 5-continued

| Organic substance | PEx. 1 (%) | PEx. 3 (%) | Ex. 6 (%) | Ex. 7 (%) | Ex. 8 (%) |
|---|---|---|---|---|---|
| Mn | 2,400 | 80 | <1.0 | <1.0 | <1.0 |
| OD$_{500}$ | 0.256 | 0.258 | 0.220 | 0.215 | 0.225 |

Pex. = Preparation Example, Ex. = Example

TABLE 6

| Organic substances | CEx. 4 (%) | CEx. 5 (%) | CEx. 6 (%) | CEx. 7 (%) |
|---|---|---|---|---|
| 2,6-NDCA | 99.721 | 99.829 | 99.960 | 99.827 |
| 2-NA | 0.006 | 0.005 | 0.005 | 0.007 |
| 2,6-MNA | 0.002 | 0.123 | 0.003 | 0.128 |
| TMAC | 0.001 | 0.003 | 0.002 | 0.002 |
| 2,6-FNA | 0.235 | 0.006 | 0.004 | 0.005 |
| TDCA | 0.000 | 0.0o1 | 0.000 | 0.002 |
| L.E. | 0.009 | 0.013 | 0.009 | 0.012 |
| Br-2,6-NDCA | 0.012 | 0.003 | 0.003 | 0.002 |
| NTCA | 0.003 | 0.003 | 0.003 | 0.002 |
| H.E. | 0.011 | 0.014 | 0.011 | 0.013 |
| Total | 100.000 | 100.000 | 100.000 | 100.000 |
| Heavy metal component | (ppm) | (ppm) | (ppm) | (ppm) |
| Mn | 5.0 | <1.0 | 50 | <1.0 |
| OD$_{500}$ | 0.230 | 0.224 | 0.450 | 0.218 |

CEx. = Comparative Example

Concerning a hue in Examples and Comparative Examples hereinafter, 1 g of a sample was dissolved in 10 ml of a 1N sodium hydroxide aqueous solution and evaluated for an absorbance of light having a wavelength of 400 nm (to be abbreviated as "OD$_{400}$" hereinafter) with a 10 mm long quartz cell.

Example 9

A pressure filtration apparatus having a volume of 300 ml was charged with 20.0 g of the crude 2,6-NDCA obtained in Preparation Example 1, 20.0 g (1.07 equivalent weights based on 2,6-NDCA) of TEA and 100 g of an acetone solution containing 10 wt % of water, and these materials were mixed at 100° C. to dissolve the 2,6-NDCA. Heavy metal components which were insolubles were removed by filtering the solution through a metal filter having openings having a diameter of 1 μm. The whole filtrate was recharged into a 300-ml autoclave equipped with a stirrer, a filtration device and a gas outlet, and the atmosphere in the autoclave was replaced with nitrogen. Then, the filtrate was stirred at 100° C. for 30 minutes. The resultant solution was cooled to 25° C. over 8 hour period to precipitate a crystal of 2,6-NDCA-TEA. The crystal of 2,6-NDCA-TEA was collected by filtration, and washed with 50 g of acetone. The recovery of the 2,6-NDCA-TEA was 96.7%.

Then, 60 g of water was added to the above crystal of 2,6-NDCA-TEA to form an aqueous solution, and the aqueous solution was heated up to 200° C. While water was added at a flow rate of 100 g/hour at the same temperature, a distillate was withdrawn, at a rate equivalent to the flow rate of water, from the top of the reaction apparatus. This procedure was carried out for 2 hours. The total distillate amount was about 21 times as much as the amount of 2,6-NDCA in the solution. Then, the solution was filtered under pressure at the same temperature to obtain a crystal of 2,6-NDCA, and the crystal of 2,6-NDCA was washed with water and with acetic acid and dried at 120° C. for 5 hours, to give 18.4 g of a purified 2,6-NDCA having a composition and a hue shown in Table 7. The recovery of the 2,6-NDCA after all the procedures was 92.1%. The so-obtained purified 2,6-NDCA had a remarkably improved hue and contained almost no organic impurities.

Example 10

The same procedures for crystallization and distilling off TEA as those in Example 9 were repeated except that 100 g of the acetone solution containing 10 wt % of water was replaced with 140 g of an acetone solution containing 5 wt % of water. As a result, 18.9 g of a purified 2,6-NDCA having a composition and a hue shown in Table 7 was obtained.

The recovery of 2,6-NDCA-TEA obtained by the crystallization was remarkably high, as high as more than 99%, and the recovery of the 2,6-NDCA after all the procedures was 94.3%.

Example 11

The same procedures for crystallization and distilling off TMA as those in Example 9 were repeated except that 20 g of TEA was replaced with 11.7 g (1.07 equivalent weights based on 2,6-NDCA) of TMA. As a result, 18.4 g of a purified 2,6-NDCA having a composition and a hue shown in Table 7 was obtained. The recovery of the 2,6-NDCA-TEA was 92.0%.

Example 12

The same procedures for crystallization and distilling off TEA as those in Example 9 were repeated except that 100 g of the acetone solution containing 10 wt % of water was replaced with 100 g of a methyl ethyl ketone solution containing 10 wt % of water. As a result, 16.0 g of a purified 2,6-NDCA having a composition and a hue shown in Table 7 was obtained.

The recovery of 2,6-NDCA-TEA obtained by the crystallization was 84.5%, or lower than that when the acetone solution containing 10 wt % of water was used, and the recovery of the 2,6-NDCA after all the procedures was 80.3%.

Example 13

The same procedures for crystallization and distilling off TEA as those in Example 9 were repeated except that 100 g of the acetone solution containing 10 wt % of water was replaced with 100 g of a cyclohexanone solution containing 10 wt % of water. As a result, 15.1 g of a purified 2,6-NDCA having a composition and a hue shown in Table 7 was obtained.

The recovery of 2,6-NDCA-TEA obtained by the crystallization was 79.3%, or lower than that when the acetone solution containing 10 wt % of water was used, and the recovery of the 2,6-NDCA after all the procedures was 75.4%.

TABLE 7

| Organic substance | Ex. 9 (%) | Ex. 10 (%) | Ex. 11 (%) | Ex. 12 (%) | Ex. 13 (%) |
| --- | --- | --- | --- | --- | --- |
| 2,6-NDCA | 99.997 | 99.968 | 99.973 | 99.972 | 99.973 |
| 2-NA | 0.000 | 0.000 | 0.001 | 0.000 | 0.000 |
| 2,6-MNA | 0.000 | 0.000 | 0.000 | 0.000 | 0.000 |
| TMAC | 0.000 | 0.000 | 0.000 | 0.000 | 0.000 |

TABLE 7-continued

| Organic substance | Ex. 9 (%) | Ex. 10 (%) | Ex. 11 (%) | Ex. 12 (%) | Ex. 13 (%) |
| --- | --- | --- | --- | --- | --- |
| 2,6-FNA | 0.000 | 0.001 | 0.001 | 0.000 | 0.000 |
| L.E. | 0.003 | 0.004 | 0.003 | 0.003 | 0.002 |
| Br-2,6-NDCA | 0.000 | 0.001 | 0.000 | 0.000 | 0.000 |
| NTCA | 0.000 | 0.003 | 0.002 | 0.003 | 0.002 |
| H.E. | 0.020 | 0.023 | 0.020 | 0.022 | 0.023 |
| Total | 100.000 | 100.000 | 100.000 | 100.000 | 100.000 |
| Heavy metal component (ppm) | (ppm) | (ppm) | (ppm) | (ppm) | (ppm) |
| Co | <1.0 | <1.0 | <1.0 | <1.0 | <1.0 |
| Mn | 3.0 | 4.3 | 3.3 | 3.2 | 3.5 |
| Hue value | ($OD_{400}$) 0.043 | ($OD_{400}$) 0.050 | ($OD_{400}$) 0.045 | ($OD_{400}$) 0.047 | ($OD_{400}$) 0.044 |

Ex. = Example

Comparative Example 8

The same procedures for crystallization and distilling off TEA as those in Example 9 were repeated except that 100 g of the acetone solution containing 10 wt % of water was replaced with 20 g of water. As a result, 8.2 g of a purified 2,6-NDCA having a composition and a hue shown in Table 8 was obtained.

The recovery of 2,6-NDCA-TEA obtained by the crystallization was very low, as low as 43.2%, and the recovery of the 2,6-NDCA after all the procedures was 41.0%.

Comparative Example 9

An attempt was made to repeat the same procedures for crystallization and distilling off TEA as those in Example 9 except that 100 g of the acetone solution containing 10 wt % of water was replaced with 100 g of acetone. However, the crude 2,6-NDCA was not at all dissolved even by heating at 100° C., and no purified 2,6-NDCA was obtained.

Comparative Example 10

An attempt was made to repeat the same procedures for crystallization and distilling off TEA as those in Example 9 except that 100 g of the acetone solution containing 10 wt % of water was replaced with 100 g of methyl ethyl ketone. However, the crude 2,6-NDCA was not at all dissolved even by heating at 100° C., and no purified 2,6-NDCA was obtained.

Comparative Example 11

20.0 Grams of the crude 2,6-NDCA obtained in Preparation Example 1 was mixed with, and dissolved in, 20.0 g (1.07 equivalent weights based on 2,6-NDCA) of TEA and 40.0 g of water at room temperature, and the solution was filtered through a filter having openings having a diameter of 1 μm to remove heavy metal components which were insolubles. While the filtrate was stirred at room temperature, 360 g of acetone was added to precipitate a crystal of 2,6-NDCA-TEA. The crystal of 2,6-NDCA-TEA was collected by filtration, and washed with 50 g of acetone. The recovery of the 2,6-NDCA-TEA at this time was 87.6%.

The above-obtained crystal of 2,6-NDCA-TEA was subjected to the same distillation as that in Example 9, to give 16.6 g of a purified 2,6-NDCA having a composition and a hue shown in Table 8. The recovery of the purified 2,6-NDCA was 83.2%. The 2,6-NDCA contained considerable amounts of impurities and showed a poor improvement in hue.

TABLE 8

| Organic substance | PEx. (%) | CEx. 8 (%) | CEx. 9 (%) | CEx. 10 (%) | CEx. 11 (%) |
|---|---|---|---|---|---|
| 2,6-NDCA | 98.593 | 99.970 | No purified 2,6-NDCA was obtained. | No purified 2,6-NDCA was Obtained. | 99.260 |
| 2-NA | 0.056 | 0.002 | | | 0.042 |
| 2,6-MNA | 0.010 | 0.000 | | | 0.008 |
| TMAC | 0.630 | 0.000 | | | 0.255 |
| 2,6-FNA | 0.263 | 0.001 | | | 0.120 |
| L.E. | 0.097 | 0.004 | | | 0.011 |
| Br-2,6-NDCA | 0.165 | 0.000 | | | 0.120 |
| NTCA | 0.164 | 0.000 | | | 0.086 |
| H.E. | 0.022 | 0.023 | | | 0.098 |
| Total | 100.000 | 100.000 | | | 100.000 |
| Heavy metal component | (ppm) | (ppm) | (ppm) | (ppm) | (ppm) |
| Co | 3,400 | <1.0 | | | <1.0 |
| Mn | 2,400 | 3.5 | | | 3.9 |
| Hue value | ($OD_{400}$) 0.930 | ($OD_{400}$) 0.061 | ($OD_{400}$) | ($OD_{400}$) | ($OD_{400}$) 0.452 |

Ex. = Example

Example 14

A pressure filtration apparatus having a volume of 300 ml was charged with 50.0 g of the crude 2,6-NDCA obtained in Preparation Example 1, 50.0 g (1.07 equivalent weights based on 2,6-NDCA) of TEA and 100 g of an acetonitrile solution containing 10 wt % of water, and these materials were mixed at 100° C. to dissolve the 2,6-NDCA. Heavy metal components which were insolubles were removed by filtering the solution through a metal filter having openings having a diameter of 1 μm. The whole filtrate was recharged into a 300-ml autoclave equipped with a stirrer, a filtration device and a gas outlet, and the atmosphere in the autoclave was replaced with nitrogen. Then, the filtrate was stirred at 100° C. for 30 minutes. The resultant solution was cooled to 25° C. over 8 hour period to precipitate a crystal of 2,6-NDCA-TEA. The crystal of 2,6-NDCA-TEA was collected by filtration, and washed with 100 g of acetonitrile twice. The recovery of the 2,6-NDCA-TEA was 95.6%. Then, 150 g of water was added to the above crystal of 2,6-NDCA-TEA to form an aqueous solution, and the aqueous solution was heated up to 200° C. While water was added at a flow rate of 200 g/hour at the same temperature and nitrogen was added to adjust the whole pressure in a reaction system at 30 kg/cm²G, a distillate was withdrawn, at a rate equivalent to the flow rate of water, from the top of the reaction apparatus. This procedure was carried out for 2 hours and a half. The total distillate amount was about 10 times as much as the amount of 2,6-NDCA in the solution. Then, the solution was filtered under pressure at the same temperature to obtain a crystal of 2,6-NDCA, and the crystal of 2,6-NDCA was washed with water and with acetic acid and dried at 120° C. for 5 hours, to give 44.5 g of a purified 2,6-NDCA having a composition and a hue shown in Table 9. The recovery of the 2,6-NDCA after all the procedures was 90.8%. The so-obtained purified 2,6-NDCA had a remarkably improved hue and contained almost no organic impurities.

Example 15

The same procedures for crystallization and distilling off TEA as those in Example 14 were repeated except that 100 g of the acetonitrile solution containing 10 wt % of water was replaced with 100 g of an acetonitrile solution containing 5 wt % of water. As a result, 46.2 g of a purified 2,6-NDCA having a composition and a hue shown in Table 9 was obtained. The recovery of 2,6-NDCA-TEA obtained by the crystallization was remarkably high, as high as more than 99%, and the recovery of the 2,6-NDCA after all the procedures was 94.3%.

Example 16

The same procedures for crystallization and distilling off TEA as those in Example 14 were repeated except that 100 g of the acetonitrile solution containing 10 wt % of water was replaced with 100 g of an acetonitrile solution containing 20 wt % of water. As a result, 41.3 g of a purified 2,6-NDCA having a composition and a hue shown in Table 9 was obtained. The recovery of 2,6-NDCA-TEA obtained by the crystallization was 88.6%, and the recovery of the 2,6-NDCA after all the procedures was 84.2%.

Example 17

The same procedures for crystallization and distilling off TMA as those in Example 14 were repeated except that 50 g of TEA was replaced with 29.3 g (1.07 equivalent weights based on 2,6-NDCA) of TMA. As a result, 44.1 g of a purified 2,6-NDCA having a composition and a hue shown in Table 9 was obtained. The recovery of the 2,6-NDCA-TEA was 90.1%.

TABLE 9

| Organic substances | Ex. 14 (%) | Ex. 15 (%) | Ex. 16 (%) | Ex. 17 (%) |
|---|---|---|---|---|
| 2,6-NDCA | 99.978 | 99.966 | 99.979 | 99.974 |
| 2-NA | 0.000 | 0.000 | 0.000 | 0.000 |
| 2,6-MNA | 0.000 | 0.000 | 0.000 | 0.000 |
| TMAC | 0.000 | 0.000 | 0.000 | 0.000 |
| 2,6-FNA | 0.000 | 0.001 | 0.000 | 0.000 |
| L.E. | 0.002 | 0.004 | 0.002 | 0.002 |
| Br-2,6-NDCA | 0.000 | 0.001 | 0.000 | 0.000 |
| NTCA | 0.000 | 0.003 | 0.000 | 0.003 |
| H.E. | 0.020 | 0.025 | 0.019 | 0.021 |
| Total | 100.000 | 100.000 | 100.000 | 100.000 |
| Heavy metal component | (ppm) | (ppm) | (ppm) | (ppm) |
| Co | <1.0 | <1.0 | <1.0 | <1.0 |
| Mn | 3.5 | 4.0 | 3.0 | 3.2 |
| Hue Value ($OD_{400}$) | 0.041 | 0.050 | 0.039 | 0.044 |

Ex. = Example

Comparative Example 12

The same procedures for crystallization and distilling off TEA as those in Example 14 were repeated except that 100 g of the acetonitrile solution containing 10 wt % of water was replaced with 50 g of water. As a result, 20.1 g of a purified 2,6-NDCA having a composition and a hue shown in Table 10 was obtained. The recovery of 2,6-NDCA-TEA obtained by the crystallization was very low, as low as 43.2%, and the recovery of the 2,6-NDCA after all the procedures was 41.0%.

Comparative Example 13

The same procedures for crystallization and distilling off TEA as those in Example 14 were repeated except that 100 g of the acetonitrile solution containing 10 wt % of water was replaced with 100 g of acetonitrile. Although these materials were mixed under heat at 100° C., the crude 2,6-NDCA was not dissolved at all. No purified 2,6-NDCA was obtained.

TABLE 10

| Organic substances | PEx. (%) | CEx. 12 (%) | CEx. 13 (%) |
|---|---|---|---|
| 2,6-NDCA | 98.593 | 99.968 | No purified 2,6-NDCA was obtained. |
| 2-NA | 0.056 | 0.001 | |
| 2,6-MNA | 0.010 | 0.000 | |
| TMAC | 0.630 | 0.000 | |
| 2,6-FNA | 0.263 | 0.002 | |
| L.E. | 0.097 | 0.004 | |
| Br-2,6-NDCA | 0.165 | 0.000 | |
| NTCA | 0.164 | 0.000 | |
| H.E. | 0.022 | 0.025 | |
| Total | 100.000 | 100.000 | |
| Heavy metal component | (ppm) | (ppm) | (ppm) |
| Co | 3,400 | <1.0 | |
| Mn | 2,400 | 3.2 | |
| Hue value ($OD_{400}$) | 0.930 | 0.045 | |

Ex. = Example

What is claimed is:

1. A process for the production of a high-purity naphthalenedicarboxylic acid, which comprises dissolving a crude naphthalenedicarboxylic acid obtained by the oxidation of dialkyl naphthalene in an aqueous solution containing an aliphatic or alicyclic amine, removing heavy metal components contained as impurities until the content of the heavy metal components based on the crude naphthalenedicarboxylic acid is 100 ppm or less, and heating the aqueous solution containing a naphthalenedicarboxylic acid amine salt to provide a high-purity naphthalenedicarboxylic acid by distilling off the amine.

2. A process according to claim 1, wherein the heavy metal components are removed by filtration or by filtration and subsequent adsorption with a solid adsorbent.

3. A process according to claim 1, wherein the aqueous solution containing a naphthalenedicarboxylic acid amine salt obtained after the heavy metal components are removed is subjected to hydrogenation and then heated to distill off the amine.

4. A process according to claim 1, wherein the aqueous solution containing a naphthalenedicarboxylic acid amine salt obtained after the heavy metal components are removed is brought into contact with a metal belonging to the group VIII of the periodic table in an inert gas atmosphere and then heated to distill off the amine.

5. A process according to claim 4, wherein the aqueous solution containing an amine salt of the naphthalenedicarboxylic acid is brought into contact with a metal belonging to the group VIII of the periodic table at a temperature of 250° C. or lower.

6. A process according to claim 4, wherein the metal belonging to the group VIII of the periodic table is at least one selected from the group consisting of Pt, Pd, Rh, Ru, Ni and Co.

7. A process according to claim 4, wherein the aqueous solution containing a naphthalenedicarboxylic acid amine salt is brought into contact with a metal belonging to the group VIII of the periodic table, then subjected to hydrogenation, and heated to distill off the amine.

8. A process according to claim 1, wherein wherein the aqueous solution containing a naphthalenedicarboxylic acid amine salt obtained after the heavy metal components are removed is subjected to crystallization in mixed solvents of water and aliphatic ketone, alicyclic ketone or acetonitrile to obtain a naphthalenedicarboxylic acid amine salt, and the naphthalenedicarboxylic acid amine salt is heated to distill off the amine.

9. A process according to claim 8, wherein the amine is distilled off by heating the naphthalenedicarboxylic acid amine salt in the co-presence of water.

10. A process according to claim 1, wherein the naphthalenedicarboxylic acid is 2,6-naphthalenedicarboxylic acid.

11. A process for the production of a high-purity naphthalenedicarboxylic acid, which comprises dissolving a crude naphthalenedicarboxylic acid obtained by the oxidation of dialkyl naphthalene in an aqueous solution containing an aliphatic or alicyclic amine, bringing the aqueous solution into contact with a metal belonging to the group VIII of the periodic table in an inert gas atmosphere, and heating the aqueous solution containing a naphthalenedicarboxylic acid amine salt to provide a high-purity naphthalenedicarboxylic acid by distilling off the amine.

12. A process according to claim 11, wherein the aqueous solution containing a naphthalenedicarboxylic acid amine salt is brought into contact with a metal belonging to the group VIII of the periodic table at a temperature of 250° C. or lower.

13. A process according to claim 11, wherein the metal belonging to the group VIII of the periodic table is at least one selected from the group consisting of Pt, Pd, Rh, Ru, Ni and Co.

14. A process according to claim 11, wherein the aqueous solution containing a naphthalenedicarboxylic acid amine salt is brought into contact with a metal belonging to the group VIII of the periodic table, then subjected to hydrogenation, and heated to distill off the amine.

15. A process for the production of a high-purity naphthalenedicarboxylic acid, which comprises dissolving a crude naphthalenedicarboxylic acid obtained by the oxidation of dialkyl naphthalene in an aqueous solution containing an aliphatic amine, an alicyclic amine or an acetonitrile, precipitating a crystal of a naphthalenedicarboxylic acid amine salt by crystallization in mixed solvents of water with an aliphatic ketone, an alicyclic ketone or an acetonitrile, and heating the naphthalenedicarboxylic acid amine salt to provide a high-purity naphthalenedicarboxylic acid by distilling off the amine.

16. A process according to claim 15, wherein the crystallization is carried out in mixed solvents having a water/aliphatic ketone, alicyclic ketone or acetonitrile weight ratio of 1~99/99~1.

17. A process according to claim 15, wherein the aliphatic ketone is acetone.

18. A process according to claim 15, wherein a the naphthalenedicarboxylic acid amine salt is crystallized and then further subjected to adsorption with a solid adsorbent.

* * * * *